United States Patent [19]

Johansen

[11] Patent Number: 5,290,938
[45] Date of Patent: Mar. 1, 1994

[54] PREPARATION OF S-(−)- AND R-(+)-N-(QUINUCLIDINYL-3)-AMIDE

[75] Inventor: Gisle L. Johansen, Sarpsborg, Norway

[73] Assignee: Chiron Laboratories A.S., Norway

[21] Appl. No.: 966,268

[22] Filed: Oct. 26, 1992

Related U.S. Application Data

[62] Division of Ser. No. 838,459, Apr. 15, 1992.

[30] Foreign Application Priority Data

Sep. 15, 1989 [NO] Norway ............................... 8393692

[51] Int. Cl.$^5$ ............................................ C07D 453/02
[52] U.S. Cl. .................................................... 546/133
[58] Field of Search ......................................... 546/133

[56] References Cited

FOREIGN PATENT DOCUMENTS 0099789 2/1984 European Pat. Off. .
0280603A1 8/1988 European Pat. Off. .

OTHER PUBLICATIONS

Mikhlina et al., Khimiko-Farmatsevtischeskij Zhurnal, 7:20-24, 1973. Translation in S. Ordzhonikidze.
All-Union Scientific-Research Institute of Pharmaceutical Chemistry, Moscow, pp. 492-496, 1974.
Mikhlina et al., Chemical Abstracts 65:2219h-2220h, 1966.

*Primary Examiner*—Marianne M. Cintins
*Assistant Examiner*—Catherine Scalzo
*Attorney, Agent, or Firm*—Fish & Richardson

[57] ABSTRACT

Optical active forms of the carboxylic acid amines of 3-aminoquinuclidine of formula (I), and the preparation thereof. These can be hydrolysed to the optical active forms of 3-aminoquinuclidine.

7 Claims, No Drawings

PREPARATION OF S-(−)- AND R-(+)-N-(QUINUCLIDINYL-3)-AMIDE

This is a divisional of copending application Ser. No. 07/838,459 filed Apr. 15, 1992.

The amides of optically active 3-aminoquinuclidine are useful precursors in the synthesis of certain gastrointestinal drugs.

From the French Patent Application 87.01355 it is known that resolution of racemic N-(quinuclidinyl-3)-chloro-3 benzamide with optically active tartaric acid yields the optically active benzamide in 32% yield from racemic benzamide. Subsequent hydrolysis of the optically active benzamide yields optically active 3-aminoquinuclidine dihydrochlorides.

The same patent also describes the asymmetric synthesis of optically active N-(α-methyl-benzyl)-3-aminoquinuclidine dihydrochlorides and the subsequent hydrolysis of these compounds to yield optically active 3-aminoquinuclidine dihydrochlorides. However, these methods are time consuming, they give low yields and the products do not have the necessary optical purity.

The present invention provides a method for resolving a racemic carboxylic acid amide of 3-aminoquinuclidine of formula (I)

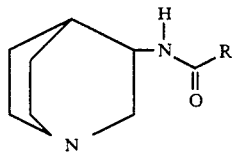

in which R is a linear or branched hydrocarbon chain of the general formula $C_nH_{(2n+1)}$, preferably $CH_3$ or $C_2H_5$.

The invention comprises of forming a salt of formula (II)

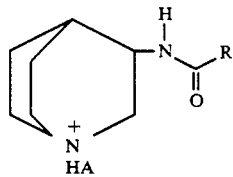

(in which R is as described earlier and HA is the chiral acid) with a chiral acid, separating the diastereomeric salts and regenerating the amide (I) in either optically active form from the separated salts.

This method gives high yields (75–80% from racemic 3-aminoquinuclidine dihydrochloride) of N-(quinuclidinyl-3)acetamide with R- or S- absolute configuration with high optical purity (up to 99,8% e.e.).

Hydrolysis of the optically active amides gives the single enantiomers of 3-aminoquinuclidine dihydrochloride in very good yields (70–75% from racemic 3-aminoquinuclidine dihydrochloride) with unusually high optical purities (better than 99,5% e.e.).

The racemic compounds of formula (I) are obtained by acylation of racemic 3-amino-quinuclidine dihydrochloride with the respective acyl chlorides or anhydrides.

The racemic and optically active compounds of formula (I) are new compounds, as well as the compounds of formula (II).

The optically active amides of formula (I) are new compounds, as well as the compounds of formula (II).

Chiral acids which may be used to make the salt (II) include S-(+)-camphor-10-sulphonic acid, R-(−)-camphor-10 sulphonic acid and their monohydrates.

The compounds of formula (II) may be formed in any convenient way.

For example, the racemic compound of formula (I) may be dissolved in a suitable solvent, such as methanol, ethanol, isopropanol, butanol or acetone, with subsequent addition of the chiral acid dissolved in a suitable solvent, such as above. The solvent used should preferably be water-miscible.

The diastereometic mixture of salts of the formula (I) may be separated by known methods. Fractional crystallisation from an inert solvent such as methanol, ethanol, isopropanol, butanol or acetone, is preferably used.

The optically active amide of formula (I) is regenerated by treatment of the resolved salt with aqueous base (e.g. KOH, NaOH, $NaHCO_3$ or $Na_2CO_3$) and extraction with a non-water-miscible solvent such as ether, chloroform or dichloromethane.

The resolved amide of the formula (I) obtained by this method may be hydrolysed with strong aqueous acid (e.g. 3–12N HCl or 10% sulphuric acid) or base (e.g. 10% NaOH) at high temperatures (e.g. 60°–110° C.) to yield optically active salt of 3-aminoquinuclidine, preferably with 6N HCl.

The following examples illustrate the invention. Optical purity was determined by gas chromatographic analysis of the diastereomeric compounds formed with optically pure α-methoxyphenylacetic acid chloride.

EXAMPLE 1

N-(Quinuclidinyl-3-)-acetamide.

Racemic 3-aminoquinuclidine dihydrochloride (10.25 kg, 51,5 mol) was dissolved in water (20 l). To this solution was added a solution of NaOH (2.05 kg, 51.3 mol) in water (2 l). The solution was cooled to 24° C. and acetic acid anhydride (6.5 kg, 63.7 mol) was added quickly. The resulting solution was stirred for two hours at 60°–28° C. before addition of additional acetic acid anhydride (0,5 kg, 4.9 mol), followed by stirring for one hour.

The pH of the solution was adjusted to 13 by addition of NaOH (6.0 kg, 150 mol) and $K_2CO_3$ (1.0 kg, 7.2 mol). This solution was extracted with $CHCl_3$ (5×20 l) and the solvent was removed in vacuo from the combined organic phases.

This gave 8.65 kg racemic N-(quinuclidinyl-3-)-acetamide, better than 98% pure, mp. 140°–141° C.

EXAMPLE 2

N-(Quinuclidinyl-3-)-propionamide.

Racemic 3-aminoquinuclidine dihydrochloride (50 g, 0.25 mol) was dissolved in water (100 ml). To this solution was added NaOH (10 g, 0.25 mol).

The solution was cooled to room temperature and propionic anhydride (50 g, 0.38 mol) was added. The resulting solution was stirred at 50°–20° C. for two hours. After adjustment of the pH of the solution to 13 by addition of NaOH, the solution was extracted with $CHCl_3$ (5×100 ml). The solvent was removed under reduced pressure from the combined organic phases.

Recrystallization of the crude product gave the title compound (37 g), better than 98% pure, mp. 96°–98° C.

EXAMPLE 3

S-N-(aminoquinuclidinyl-3)-acetamide-L-(−)-camphor-10-sulphonate.

A solution of L-(−)-camphor-10-sulphonic acid monohydrate (3.4 kg, 13.6 mol) in acetone (17 l) was added to a solution of N-quinuclidinyl-3)-acetamide (4.8 kg, 28.6 mol) in acetone (14 l).

The mixture was cooled to 30° C. with stirring, filtered and the solid washed with acetone (2×2.5 l). Drying of the solid yielded S-(−)-N-(aminoquinuclidinyl-3)-acetamide-L-(−)-camphor-10-sulphonate (4.36 kg), mp. 211°–214° C. with an optical purity of 90%.

The crude product (5.1 kg) was dissolved in isopropanol (28 l) heated at reflux, cooled to 20° C. and worked up as above, yielding the title compound (4.26 kg) m. 218°–220° C., $[\alpha]_D^{20}=25.6°$ (c=2, water) with an optical purity of 99.5%.

EXAMPLE 4

S-N-(aminoquinuclidinyl-3)-acetamide-L-(−)-camphor-10-sulphonate.

A solution of L-(−)-camphor-10-sulphonic acid monohydrate (6.5 kg, 28.0 mol) in acetone (34 l) was added to a solution of N-quinuclidinyl-3)-acetamide (8.65 kg, 51.5 mol) in acetone (10 l).

The mixture was slowly cooled to 15° C. with stirring. After 10 hours the precipitate was filtered and washed with acetone (2×3 l) and dried.

This yielded S-(−)-N-(aminoquinuclidinyl-3)-acetamide-L-(−)-camphor-10-sulphonate (8.23 kg) mp. 218°–222° C. with an optical purity of 97.8%.

Recrystallization of this salt (8.23 kg) in isopropanol heated at reflux (45 l), yielded the title compound (7.2 kg), mp. 220°–222° C., with an optical purity of 99.9%. This corresponds to 99.8% ee.

EXAMPLE 5

R-N-(aminoquinuclidinyl-3)-acetamide-D-(+)-camphor-10-sulphonate

The mother liqueur from the first precipitation in Example 3 was evaporated to a total volume of 20 l and added a solution of D-(+)-camphor-10-sulphonic acid (3.4 kg, 14.7 mol) in acetone (17 l).

The mixture was worked up as in Example 3, yielding R-(+)-N-(aminoquinuclidinyl-3)-acetamide-D-(+)-camphor-10-sulphonate (4.94 kg), mp. 207°–210° C. with an optical purity of 80%. This crude product was dissolved in isopropanol (22.5 l) heated at reflux, cooled to 20° C. with stirring and worked up as above, yielding R-(+)-N-(aminoquinuclidinyl-3)-acetamide-D-(+)-camphor-10-sulphonate (4.05 kg), mp. 215°–217° C., $[\alpha]_D^{20}=24.0°$ (c=2, water) with an optical purity of 99.2%.

EXAMPLE 6

S-N-(quinuclidinyl-3)-acetamide

The title compound from Example 3 (4.80 kg) was dissolved in a solution of NaOH (2.1 kg) and Na$_2$CO$_3$ (1.5 kg) in water (24 l).

The aqueous phase was extracted with chloroform (9×10 l) and the combined extracts dried over MgSO$_4$. Removal of the solvent under reduced pressure yielded S-(−)-N-(quinuclidinyl-3)-acetamide (1.80 kg) mp. 128°–131° C. (with sintering), $[\alpha]_D^{20}=-50.0°$ (c=2, CHCl$_3$) with an optical purity of 99.5%.

EXAMPLE 7

R-N-(Quinuclidinyl-3)-acetamide

The title compound from Example 5 (4.00 kg) was dissolved in an aqueous solution of NaOH (1.76 kg) and Na$_2$CO$_3$ (1.4 kg).

The aqueous phase was extracted with chloroform (9×10 l) and worked up as above, yielding R-(+)-N-(quinuclidinyl-3)acetamide (1.41 kg), mp. 128°–130° C. (with sintering), $[\alpha]_D^{20}=+49.5°$ (c=2, CHCl$_3$) with an optical purity of 99.3%.

EXAMPLE 8

8-3-Aminoquinuclidine dihydrochloride

The title compound from Example 6 (1.80 kg) was dissolved in water (2.5 l), to this solution was added 37% HCl (4.5 l). This mixture was heated at reflux for 3 hours while water and acetic acid (3 l) was distilled off. The residue was evaporated under reduced pressure to approx. 3 liter and treated with absolute ethanol and acetone.

The precipitated S-(−)-3-aminoquinuclidine dihydrochloride was filtered off and washed with absolute ethanol (2×300 ml) before drying under reduced pressure at 60° C.

This yielded the title compound (1.96 kg) mp. 310°–315° C. with an optical purity of 99.4% $[\alpha]_D^{20}=-23.5°$ (c=1, water), −40.9° (c=1, 10% NaOH).

EXAMPLE 9

R-3-Aminoquinuclidine dihydrochloride

The title compound from Example 7 (1.41 kg) was hydrolysed and worked up as in example 8, yielding R-(+)-3-aminoquinuclidine dihydrochloride (1.53 kg)mp. 311°–315° C. with an optical purity of 99.2%. $[\alpha]_D^{20}=+23.6°$ (c=1, water), 40.6° (c=1, 10% NaOH).

EXAMPLE 10

S-N-(aminoquinuclidinyl-3)-propionamide-L-(−)camphor-10-sulphonate

A solution of L-(−)-camphor-10-sulphonic acid monohydrate (10.5 g, 0.045 mol) in acetone (60 ml) was added to a solution of N-quinuclidinyl-3)-propionamide (15 g, 0.81 mol) in acetone (40 ml).

The mixture was cooled to room temperature with stirring, filtered and the solid washed with acetone (15 ml). Drying of the solid yielded S-(−)-N-(aminoquinuclidinyl-3)-propionamide-L-(−)-camphor-10-sulponate (15.9 g, 0.038 mol), mp 206°–209° C.

The crude product was dissolved in isopropanol (70 ml), heated at reflux, cooled to room temperature and worked up as above, yielding the title compound (12.1 g), mp 217°–219° C., $[\alpha]^{20}_D=-28.8°$ (c=2, water) with an optical purity of 99.5%.

EXAMPLE 11

R-N-(aminoquinuclidinyl-3)-propionamide-D-(+)-camphor-10-sulphonate

To the mother liqueur from the first precipitation in Example 10 was added a solution of D-(+)-camphor-10 sulphonic acid (10.5 g, 0.045 mol). The mixture was worked up as in Example 10, yielding R-(+)-N-

(aminoquinuclidinyl-3)-propionamide-D-(+)-camphor-10-sulphonate (14.0 g, 0.033 mol), mp 215°-217° C.

This crude product was dissolved in refluxing isopropanol (65 ml), cooled to room temperature with stirring and worked up as above, yielding the title compound (11.3 g) mp. 215°-217° C., $[\alpha]_D^{20} = +22.7°$ (c=2, water) with an optical purity of 99.5%.

EXAMPLE 12

S-N-(quinuclidinyl-3)-propionamide

The title compound from Example 10 (10 g, 0.024 mol) was dissolved in water (50 ml) containing NaOH (4.3 g, 0.11 mol) and Na$_2$CO$_3$ (3.1 g). The aqueous phase was extracted with chloroform (5×10 ml) and the combined extracts dried over MgSO$_4$.

Removal of the solvent under reduced pressure yielded S-(−)-N-(quinuclidinyl-3)-propionamide (4.7 g), mp. 111°-114° C., $[\alpha]_D^{20} = -45.7°$ (c=2, CHCl$_3$) an optical purity of 99.5%.

EXAMPLE 13

R-N-(Quinuclidinyl-3)-propionamide

The title compound from Example 11 (10 g) was worked up as in Example 12.

This yielded R-(+)-N-(quinuclidinyl)-3)-propionamide (4,5 g), mp. 111°-114° C., $[\alpha]_D^{20} = +49.7°$ (c=2, CHCl$_3$) with an optical purity of 99.5%.

EXAMPLE 14

S-3-Aminoquinuclidine dihydrochloride

The title compound from Example 12 (4.14 g) was dissolved in 6N HCl (50 ml) and heated at 100° C. for 18 hours. Water and HCl was removed under reduced pressure and the crude product treated with absolute ethanol (25 ml), filtered and dried.

This gave S-(−)-3-aminoquinuclidine dihydrochloride (4.4 g), mp. 310°-315° C. with an optical purity of 99.5%. $[\alpha]_D^{20} = -39.6°$ (c=1, 10% NaOH).

EXAMPLE 15

R-3-Aminoquinuclidine dihydrochloride.

The title compound from Example 13 (3.93 g) was treated as in Example 14, yielding R-(+)-3-aminoquinuclidine dihydrochloride (4.05 g), mp. 310°-315° C. with an optical purity of 99.5%, $[\alpha]_D^{20} = +40.6°$ (c=1, 10% NaOH).

I claim:

1. Process of preparing optically active stereo-isomeric forms of a racemic carboxylic acid amide of 3-aminoquinuclidine of the formula (I):

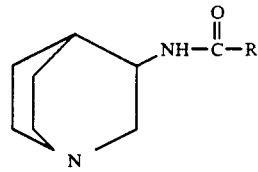

wherein R means a straight or branched hydrocarbon chain of the general formula $C_nH_{(2n+1)}$ wherein n is an integer 1 to 6, comprising the steps of
preparing a racemic aminoamidechiral acid salt of the formula (II):

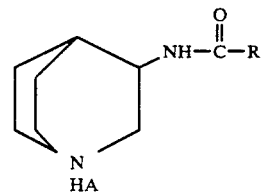

wherein R is as defined above and HA is S-(+)-camphor-10-sulphonic acid or R-(−)-camphor-10-sulphonic acid by mixing a solution of said acid with a solution of the amide of formula (I);
resolving the diastereomer salt in its optically active forms; and
releasing the amide of formula (I) in the optically active form from the separated salt.

2. The process of claim 1, wherein R is CH$_3$.

3. The process of claim 1 or 2, wherein the salts of the formula (II) are separated by fractional crystallization.

4. A process of preparing S-(−)-3-aminoquinuclidine or salts thereof, comprising hydrolyzing the enantiomer of absolute configuration 3-S of the formula (I):

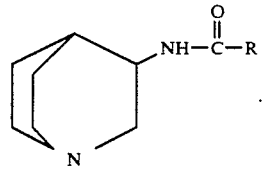

5. A process of preparing R-(+)-3-aminoquinuclidine or salts thereof, comprising hydrolyzing the enantiomer of configuration 3-R of the formula (I):

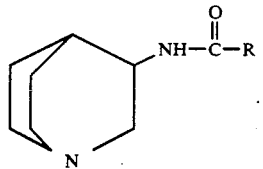

6. The process of claim 4, wherein S-(−)-N-(aminoquinuclidinyl)-3-acetamide is hydrolyzed.

7. The process of claim 5, wherein R-(+)-N-(aminoquinuclidinyl)-3-acetamide is hydrolyzed.

* * * * *